United States Patent
Deconinck et al.

(10) Patent No.: US 9,248,080 B2
(45) Date of Patent: Feb. 2, 2016

(54) PROCESS FOR BLEACHING KERATIN FIBRES COMPRISING THE APPLICATION OF A COMPOSITION IN COMPRESSED FORM

(75) Inventors: Gautier Deconinck, Saint Gratien (FR); Jean-Marc Ascione, Paris (FR); Delphine Allard, Paris (FR)

(73) Assignee: L'OREAL, Paris (FR)

(*) Notice: Subject to any disclaimer, the term of this patent is extended or adjusted under 35 U.S.C. 154(b) by 0 days.

(21) Appl. No.: 14/118,650

(22) PCT Filed: May 15, 2012

(86) PCT No.: PCT/EP2012/058988
§ 371 (c)(1),
(2), (4) Date: Nov. 19, 2013

(87) PCT Pub. No.: WO2012/159929
PCT Pub. Date: Nov. 29, 2012

(65) Prior Publication Data
US 2014/0082857 A1 Mar. 27, 2014

Related U.S. Application Data

(60) Provisional application No. 61/513,603, filed on Jul. 31, 2011, provisional application No. 61/513,604, filed on Jul. 31, 2011.

(30) Foreign Application Priority Data

May 20, 2011 (FR) ...................................... 11 54421
May 20, 2011 (FR) ...................................... 11 54424

(51) Int. Cl.
| | |
|---|---|
| *A61Q 5/08* | (2006.01) |
| *A61K 8/23* | (2006.01) |
| *A61K 8/22* | (2006.01) |
| *A61K 8/24* | (2006.01) |
| *A61K 8/02* | (2006.01) |
| *A61Q 5/10* | (2006.01) |

(52) U.S. Cl.
CPC .................. *A61K 8/23* (2013.01); *A61K 8/0216* (2013.01); *A61K 8/22* (2013.01); *A61K 8/24* (2013.01); *A61Q 5/08* (2013.01); *A61Q 5/10* (2013.01)

(58) Field of Classification Search
CPC ........... A61Q 5/08; A61K 8/022; A61K 8/22; A61K 8/23

USPC .................. 8/107, 109, 110, 111; 424/62
See application file for complete search history.

(56) References Cited

U.S. PATENT DOCUMENTS

| | | | |
|---|---|---|---|
| 3,376,110 | A | 4/1968 | Shiraeff |
| 3,726,967 | A | 4/1973 | Vorsatz et al. |
| 3,915,921 | A | 10/1975 | Schlatzer, Jr. |
| 4,509,949 | A | 4/1985 | Huang et al. |
| 4,540,510 | A | 9/1985 | Karl |
| 5,008,093 | A | 4/1991 | Merianos |
| 5,183,901 | A | 2/1993 | Login et al. |
| 5,279,313 | A | 1/1994 | Clausen et al. |
| 5,447,654 | A | 9/1995 | Millequant et al. |
| 5,650,091 | A | 7/1997 | Millequant et al. |
| 5,674,476 | A | 10/1997 | Clausen et al. |
| 6,379,401 | B1 | 4/2002 | Legrand et al. |
| 6,488,918 | B2 * | 12/2002 | Hess et al. ...................... 424/62 |
| 7,740,663 | B2 * | 6/2010 | De La Mettrie et al. .......... 8/107 |
| 2005/0129652 | A1 * | 6/2005 | Keller et al. ............... 424/70.14 |

FOREIGN PATENT DOCUMENTS

| | | | |
|---|---|---|---|
| DE | 102006016817 A1 * | 10/2007 | ............... A61K 8/19 |
| EP | 0216479 A1 | 4/1987 | |
| EP | 0619114 A1 | 10/1994 | |
| EP | 1602356 A1 | 12/2005 | |
| FR | 2788976 A1 | 8/2000 | |
| JP | 2010173982 A | 8/2010 | |
| WO | 2007115657 A2 | 10/2007 | |

OTHER PUBLICATIONS

English translation of the Patent DE 10206016817 A1 dated Jul. 17, 2014.*
Partial International Search Report for PCT/EP2012/058988.
Fonnum, G., et al., "Associative Thickeners. Part I: Synthesis, Rheology and Aggregation Behavior," Colloid & Polymer Science, 271, (1993), pp. 380-389.
English abstract for EP1602356 (Dec. 7, 2005).
English abstract for JP2010173982 (Aug. 12, 2010).

* cited by examiner

*Primary Examiner* — Eisa Elhilo
(74) *Attorney, Agent, or Firm* — The Marbury Law Group, PLLC

(57) ABSTRACT

The present invention relates to a process for bleaching keratin fibers which consists in applying to the keratin fibers a composition A, which is in compressed form, comprising at least one persulfate, in the presence of an aqueous composition B.

24 Claims, No Drawings

PROCESS FOR BLEACHING KERATIN FIBRES COMPRISING THE APPLICATION OF A COMPOSITION IN COMPRESSED FORM

This is a national stage application of PCT/EP2012/058988, filed internationally on May 15, 2012, which claims priority to U.S. Provisional Application Nos. 61/513,603 and 61/513,604, both filed on Jul. 31, 2011, as well as French Application Nos. 1154421 and 1154424, both filed on May 20, 2011.

The present invention relates to a process for bleaching keratin fibres, in particular the hair, using a composition A in compressed form comprising at least one persulfate, in the presence of an aqueous composition B.

The bleaching of human keratin fibres, and more particularly the hair, is performed by oxidation of the "melanin" pigment resulting in the dissolution and the partial or total removal of this pigment.

To bleach the hair, use is especially made of bleaching powders containing a peroxygenated reagent such as ammonium or alkali metal persulfates, perborates and percarbonates, which are combined at the time of use with an aqueous hydrogen peroxide composition. Since peroxygenated salts and hydrogen peroxide are relatively inefficient in acidic medium, it is often necessary to activate them at basic pH in order to obtain an adequate formation of active oxygen. It is thus common practice to add to the bleaching powders alkaline compounds such as alkali metal or alkaline-earth metal silicates and dibasic or tribasic phosphates, and in particular alkali metal metasilicates, optionally in the presence of ammonia precursors such as ammonium salts. However, bleaching powders have a tendency to form dust during their handling, transportation and storage.

Now, the products of which they are composed (alkali metal persulfates and silicates) are aggressive and in particular irritant to the eyes, the respiratory pathways and mucous membranes.

To overcome the problem of the volatility of bleaching powders, less volatile powders have been developed by adding additives for reducing the content of fine particles, and pastes have been developed comprising the said pulverulent agents (peroxygenated salts, alkaline agents, thickeners) in an organic inert liquid support. However, these less volatile powders and these pastes may prove to be less effective than the simple starting powders. Moreover, pastes, just like powders, nevertheless require certain precautions during their handling, especially as regards weighing them out in order to mix them with the oxidizing, composition, so as to avoid staining clothing.

The aim of the present invention is to provide a composition for bleaching keratin fibres that can solve the problems of the handling of the compositions known in the prior art, in particular a composition for bleaching keratin fibres that is in compressed form, to be mixed directly at the time of use with an aqueous composition.

This composition makes it possible to avoid the handling problems linked to the volatility of the powders or the weighing-out problems by proposing a product in a solid compact and ready-to-use form, without a step of metering out. It also makes it possible to improve the resistance of the composition for bleaching keratin fibres to temperature variations, and in particular makes it possible to avoid the problem of destabilization on storage at low temperatures and during transportation including temperature cycles. It also makes it possible to avoid losses of lightening power.

These aims are achieved with the present invention, one subject of which is a process for bleaching keratin fibres which consists in applying to the keratin fibres a composition A that is in compressed form comprising at least one persulfate, in the presence of an aqueous composition B.

The composition according to the invention is in compressed or compacted form, i.e. it has been obtained via a process of compression (or compacting) of particles, especially by compression or compacting of a powder or granules.

Preferably, composition A in compressed form according to the invention has at least one dimension greater than 6 mm, preferably greater than or equal to 8 mm and preferably greater than or equal to 10 mm.

In particular, it has at least one smaller dimension and at least one larger dimension, at least one of the dimensions being greater than 6 mm, preferably greater than or equal to 8 mm and preferably greater than or equal to 10 mm.

The composition according to the invention may be in compressed form, in particular in the form of a lozenge, a pastille, a tablet, etc., which may have flat or curved, concave or convex upper and lower faces and of round, oval, square, rectangular, octagonal or polygonal shape.

According to one embodiment, the composition in compressed form may be, for example, in the form of a pastille or tablet of round shape, and may have a diameter ranging from 1 to 5 cm and in particular from 2 to 4 cm and a thickness ranging from 1 to 20 mm and in particular from 3 to 10 mm.

According to one embodiment, the composition in compressed form may have a length ranging from 1 to 10 cm, a width ranging from 0.5 to 5 cm and a thickness ranging from 0.5 to 20 mm and in particular from 1 to 10 mm.

The composition in compressed form according to the invention may have a mass ranging from 0.5 to 20 g, in particular from 5 to 15 g.

A subject of the present invention is also a multi-compartment device comprising:
 a composition A that is in compressed form comprising at least one persulfate, and
 an aqueous composition B,
the said compositions being conditioned in separate compartments.

The invention also relates to a composition for bleaching keratin fibres that is in compressed form comprising at least one persulfate and at least one water-soluble silicate.

Unless otherwise indicated, the limits of the ranges of values that are given in the context of the present invention are included in these ranges.

In the text hereinabove or hereinbelow, the term "at least one" is equivalent to "one or more".

Persulfates

The composition A used in the process according to the invention comprises at least one persulfate as peroxygenated salt. Preferably, the persulfate(s) are chosen from sodium, potassium and ammonium persulfates, and mixtures thereof.

The concentration of persulfates in composition A in accordance with the invention is generally between 10% and 80% by weight, preferably between 20% and 65% by weight and better still between 40% and 60% by weight relative to the total weight of composition A.

Alkaline Agent

According to one embodiment the composition A used in the process according to the invention comprises at least one alkaline agent.

The alkaline agent(s) may be chosen, for example, from dibasic or tribasic ammonium phosphate, water-soluble silicates such as alkali metal or alkaline-earth metal silicates, for instance sodium disilicate, sodium metasilicate, dibasic or tribasic alkali metal or alkaline-earth metal phosphates or carbonates of alkali metals or alkaline-earth metals, such as lithium, sodium, potassium, magnesium, calcium and barium, and mixtures thereof. Preferably, the alkaline agent (s) are chosen from water-soluble silicates such as alkali metal or alkaline-earth metal silicates, dibasic or tribasic alkali metal or alkaline-earth metal phosphates, and alkali metal or alkaline-earth metal carbonates, and mixtures thereof.

In the context of the invention, the term "water-soluble silicate" means a silicate which has a solubility in water of greater than 0.5% preferably greater than 1% weight at 25° C. These water-soluble silicates differ from aluminium silicates and derivatives thereof, especially clays, such as mixed silicates of natural or synthetic origin that are insoluble in water.

The presence of water-soluble silicate in the bleaching composition in compressed form makes it possible to avoid the addition of an alkaline agent at the time of mixing with the oxidizing composition, and makes it possible to improve the homogeneity of the mixture with the oxidizing composition.

When they are present in the composition A in accordance with the invention, the concentration of alkaline agents is generally between 0.1% and 40% by weight, preferably between 0.5% and 30% by weight and better still between 1% and 25% by weight relative to the total weight of the composition A.

Rheology Modifiers

According to one embodiment, the composition A of the process according to the invention advantageously comprises at least one rheology modifier chosen from hydrophilic thickeners, amphiphilic polymers comprising at least one hydrophobic chain, and fillers, and mixtures thereof.

The rheology modifier(s) may be present in composition A in a content ranging from 0.01% to 30% by weight and preferably ranging from 0.1% to 10% by weight relative to the total weight of composition A.

As examples of hydrophilic thickeners, i.e. thickeners not comprising a C6-C30 hydrocarbon-based fatty chain, which may be used according to the invention, mention may be made especially of:
thickening polymers of natural origin such as
a) algal extracts, such as alginates (for instance alginic acid and sodium alginates), carrageenans and agar agars, and mixtures thereof. Examples of carrageenans that may be mentioned include Satiagum UTC30® and UTC10® from the company Degussa; an alginate that may be mentioned is the sodium alginate sold under the name Kelcosol® by the company ISP;
b) gums, such as xanthan gum, guar gum and nonionic derivatives thereof (hydroxypropyl guar), gum arabic, konjac gum or mannan gum, gum tragacanth, ghatti gum, karaya gum or locust bean gum; agar gum, and scleroglucan gums, and mixtures thereof;
c) starches, preferably modified starches, such as those derived, for example, from cereals such as wheat, corn or rice, from legumes such as yellow peas, from tubers such as potatoes or manioc, and tapioca starches; carboxymethylstarch. Examples of starches that may be mentioned include the corn starch Starx 15003 sold by the company Staley, the pregelatinized starch sold under the name Lycatab PGS by the company Roquette; the sodium carboxymethylstarch sold under the reference Explotab by the company Roquette;
d) dextrins, such as dextrin extracted from corn;
e) celluloses such as microcrystalline cellulose, amorphous cellulose and cellulose derivatives, in particular $(C_1-C_6)$hydroxyalkylcelluloses and $(C_1-C_6)$carboxyalkylcelluloses, which are in particular crosslinked; mention may be made especially of methylcelluloses, hydroxyalkylcelluloses, ethylhydroxyethylcelluloses and carboxymethylcelluloses. Examples that may be mentioned include the microcrystalline cellulose sold under the name Avicel PH 100 or PH 102 by the company FMC Biopolymers, and the cetyl hydroxyethylcelluloses sold under the names Polysurf 67CS® and Natrosol Plus 330® from Aqualon;
f) pectins,
g) chitosan and derivatives thereof,
h) anionic polysaccharides other than starch and cellulose derivatives, in particular of biotechnological origin, such as anionic polysaccharide bearing as repeating unit a tetrasaccharide composed of L-fucose, D-glucose and glucuronic acid, such as the product bearing the INCI name Biosaccharide Gum-4 sold under the reference Glycofilm 1.5P by the company Solabia,
i) soybean polysaccharides,
and mixtures thereof.
synthetic polymers such as crosslinked or non-crosslinked polyvinylpyrrolidone, for instance crosslinked polyvinylpyrrolidone, for instance Kollindon CL sold by the company BASF, acrylic acid polymers and salts thereof, for instance crosslinked polyacrylates such as the product sold by the company Röhm & Haas under the name Acusol 772, polyacrylamides, crosslinked or non-crosslinked poly-2-acrylamidopropanesulfonic acid polymers (in particular homopolymers), for instance non-crosslinked poly-2-acrylamidopropanesulfonic acid (Simulgel® EG from the company SEPPIC), crosslinked poly-2-acrylamido-2-methylpropanesulfonic acid, in free form or partially neutralized with ammonia (Hostacerin® AMPS from the company Clariant), mixtures of non-crosslinked poly-2-acrylamido-2-methylpropanesulfonic acid with hydroxyalkylcellulose ethers or with poly(ethylene oxides) as described in U.S. Pat. No. 4,540,510; mixtures of poly(meth)acrylamido $(C_1-C_4)$alkylsulfonic acid, preferably crosslinked, with a crosslinked copolymer of maleic anhydride and of a $(C_1-C_5)$alkyl vinyl ether (Stabileze QM from the company ISF), and mixtures thereof.

The amount of hydrophilic thickeners present in composition A may be between 0.01% and 30% and preferably between 0.1% and 15% by weight and better still between 0.1% and 10% by weight relative to the total weight of composition A.

The composition A of the process according to the invention may comprise at least one amphiphilic polymer comprising at least one hydrophobic chain.

More especially, if they are present, these amphiphilic polymers are of nonionic, anionic, cationic or amphoteric type. They are preferably of nonionic, anionic or cationic nature.

The said amphiphilic polymers comprise, more particularly, as hydrophobic chain, a saturated or unsaturated, aromatic or non-aromatic, linear or branched $C_6-C_{30}$ hydrocarbon-based chain, optionally attached to one or more oxyalkylene (oxyethylene and/or oxypropylene) units.

Among the cationic amphiphilic polymers comprising a hydrophobic chain are cationic polyurethanes or cationic copolymers comprising vinyllactam and in particular vinylpyrrolidone units.

Even more preferentially, the amphiphilic polymers comprising a hydrophobic chain are of nonionic or anionic nature.

Examples of hydrophobic-chain nonionic amphiphilic polymers that may be mentioned, inter alia, include celluloses comprising a hydrophobic chain (Natrosol Plus Grade 330 CS® from the company Aqualon; Bermocoll EHM 100® from the company Berol Nobel; Amercell Polymer HM-1500® from the company Amerchol); hydroxypropyl guars modified with one or more hydrophobic groups (Jaguar XC-95/3®, RE210-18, RE205-1 from the company Rhodia Chimie; Esaflor HM 22® from the company Lamberti); copolymers of vinylpyrrolidone and of hydrophobic-chain monomers (certain products of the Antaron® and Ganex® ranges from the company ISP); copolymers of $C_1$-$C_6$ alkyl (meth)acrylates and of amphiphilic monomers comprising a hydrophobic chain; copolymers of hydrophilic (meth)acrylates and of monomers comprising at least one hydrophobic chain (polyethylene glycol methacrylate/lauryl methacrylate copolymer); polymers with an aminoplast backbone containing at least one fatty chain (Pure Thix® from the company Süd-Chemie); polyether polyurethanes, of linear (block structure), grafted or star form, comprising in their chain at least one hydrophilic block and at least one hydrophobic block (as described in the article by G. Fonnum, J. Bakke and Fk. Hansen—Colloid Polym. Sci. 271, 380-389 (1993); in particular, the polyether polyurethane that may be obtained by polycondensation of at least three compounds comprising (i) at least one polyethylene glycol comprising from 150 to 180 mol of ethylene oxide, (ii) a polyoxyethylenated stearyl alcohol comprising 100 mol of ethylene oxide and (iii) a diisocyanate, such as the product sold especially by the company Elementis under the name Rheolate FX 1100®, which is a polycondensate of polyethylene glycol containing 136 mol of ethylene oxide, polyoxyethylenated stearyl alcohol containing 100 mol of ethylene oxide and hexamethylene diisocyanate (HDI) with a weight-average molecular weight of 30 000 (INCI name: PEG-136/Steareth-100I/SMDI Copolymer). Mention may also be made of Rheolate® 205, 208, 204 or 212 from the company Rheox; Elfacos® T210, T212 from the company Akzo). As examples of anionic amphiphilic polymers comprising at least one hydrophobic chain that may be used in the context of the present invention, mention may be made of crosslinked or non-crosslinked polymers comprising at least one hydrophilic unit derived from one or more ethylenically unsaturated monomers comprising a carboxylic acid function, which is free or partially or totally neutralized, and at least one hydrophobic unit derived from one or more ethylenically unsaturated monomers bearing a hydrophobic side chain, and optionally at least one crosslinking unit derived from one or more polyunsaturated monomers.

Mention may be made especially of copolymers of (meth)acrylic acid and of $C_{10}$-$C_{30}$ alkyl(meth)acrylates, which are crosslinked or non-crosslinked, such as those described in U.S. Pat. No. 3,915,921 and U.S. Pat. No. 4,509,949, or copolymers of (meth)acrylic acid and of fatty alcohol allyl ethers such as those described in EP 216 479.

In addition, the products Carbopol ETD-2020® and 1382®, Pemulen TR1® and TR2® from the company Goodrich; the methacrylic acid/ethyl acrylate/oxyethylenated stearyl methacrylate copolymer (55/35/10); the (meth)acrylic acid/ethyl acrylate/oxyethylenated behenyl methacrylate 25 EO copolymer; the methacrylic acid/ethyl acrylate/steareth-10 allyl ether crosslinked copolymer, are polymers that are suitable for use in the invention.

When these amphiphilic polymers comprising at least one hydrophobic chain are present, their content represents from 0.01% to 30% by weight and preferably from 0.1% to 10% by weight relative to the weight of composition A.

The composition A of the process according to the invention may comprise at least one filler.

The term "fillers" should be understood as meaning solid particles that are insoluble in the medium of the composition, irrespective of the temperature at which the composition is manufactured.

The fillers may be colourless or white and inorganic or organic, of any physical shape (platelet, spherical or oblong) and of any crystallographic form (for example sheet, cubic, hexagonal, orthorhombic, etc.). The fillers may be porous or non-porous.

Fillers that may be mentioned include mineral fillers such as hydrophobic or hydrophilic silicas, clays other than those mentioned above, ceramic beads, calcium carbonate, titanium oxides, magnesium oxides, aluminium silicates and derivatives thereof, especially clays, such as mixed silicates of natural or synthetic origin, in particular magnesium aluminium silicates, which are especially hydrated, natural hydrated aluminium silicates, such as bentonite or kaolin, talc, organic fillers such as Nylon, microspheres based on a copolymer of vinylidene chloride/acrylonitrile/methacrylonitrile containing isobutane, and expanded, such as those sold under the name Expancel 551 DE® by the company Expancel, micronized vegetable powder (such as the fruit powders from the company Lessonia) or non-micronized vegetable powder, or alternatively rice grain husk powder, and mixtures thereof.

Among the silicas, mention may also be made in particular of fumed silicas of hydrophilic nature (especially Aerosil® 90, 130, 150, 200, 300 and 380 from the company Degussa Hüls).

The filler content may range from 0.01% to 30% by weight, preferably from 0.05% to 20% by weight and better still from 0.1% to 10% by weight relative to the total weight of composition A.

Some of the rheology modifiers mentioned above may also play a role in aiding the disintegration of composition A in compressed form during its use.

Thus, in one particular embodiment, the composition A of the process according to the invention comprises at least one agent chosen from celluloses and cellulose derivatives, crosslinked polyacrylates, crosslinked polyvinylpyrrolidone, gums, such as guar gum, soybean polysaccharides, alginates, aluminium silicates and derivatives thereof, and silicas, in particular hydrophilic silicas, and mixtures thereof.

Surfactants

The composition A of the process according to the invention may advantageously comprise at least one surfactant.

The surfactant(s) may be chosen indiscriminately, alone or as mixtures, from anionic, amphoteric, nonionic, zwitterionic and cationic surfactants, in particular from anionic and/or nonionic surfactants.

The surfactants suitable for implementing the present invention are in particular the following:

Among the nonionic surfactants, mention may be made of alcohols, alpha-diols and alkyl phenols, each of these compounds being polyethoxylated and/or polypropoxylated, and containing at least one hydrocarbon-based chain comprising, for example, from 8 to 30 carbon atoms and preferably from 8 to 18 carbon atoms, the number of ethylene oxide and/or propylene oxide groups possibly ranging especially from 2 to 50.

Mention may also be made of copolymers of ethylene oxide and propylene oxide, condensates of ethylene oxide and of propylene oxide with fatty alcohols; polyethoxylated fatty amides preferably having from 2 to 30 mol of ethylene oxide, ethoxylated fatty acid esters of sorbitan containing from 2 to 30 mol of ethylene oxide, fatty acid esters of sucrose, fatty acid esters of polyethylene glycol, alkylpolyglycosides, N-alkylglucamine derivatives, etc.

The term "anionic surfactant" means a surfactant comprising, as ionic or ionizable groups, only anionic groups. These anionic groups are preferably chosen from the groups $CO_2H$, $CO_2^-$, $SO_3H$, $SO_3^-$, $OSO_3H$, $OSO_3^-$, $O_2PO_2H$, $O_2PO_2H^-$ and $O_2PO_2^{2-}$.

The anionic surfactant(s) that may be used in the compositions of the invention are chosen in particular from alkyl sulfates, alkyl ether sulfates, alkylamido ether sulfates, alkylaryl polyether sulfates, monoglyceride sulfates, alkylsulfonates, alkylamide sulfonates, alkylarylsulfonates, α-olefin sulfonates, paraffin sulfonates, alkylsulfosuccinates, alkyl ether sulfosuccinates, alkylamide sulfosuccinates, alkyl sulfoacetates, acylsarcosinates, acylglutamates, alkylsulfosuccinamates, acylisethionates and N-acyltaurates, salts of alkyl monoesters and polyglycoside-polycarboxylic acids, acyllactylates, salts of D-galactoside uronic acids, salts of alkyl ether carboxylic acids, salts of alkyl aryl ether carboxylic acids, and salts of alkylamido ether carboxylic acids; or the non-salified forms of all of these compounds, the alkyl and acyl groups of all of these compounds containing from 6 to 24 carbon atoms and the aryl group denoting a phenyl group.

Some of these compounds may be oxyethylenated and then preferably comprise from 1 to 50 ethylene oxide units.

The salts of C6-C24 alkyl monoesters of polyglycoside-polycarboxylic acids may be chosen from C6-C24 alkyl polyglycoside citrates, C6-C24 alkyl polyglycoside-tartrates and C6-C24 alkyl polyglycoside-sulfosuccinates.

When the anionic surfactant(s) are in salt form, they may be chosen from alkali metal salts such as the sodium or potassium salt and preferably the sodium salt, the ammonium salts, the amine salts and in particular amino alcohol salts or the alkaline-earth metal salts such as the magnesium salt.

Examples of amino alcohol salts that may especially be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts.

Alkali metal or alkaline-earth metal salts, and in particular sodium or magnesium salts, are preferably used.

Use is preferably made of (C6-C24)alkyl sulfates and (C6-C24)alkyl ether sulfates, which are optionally oxyethylenated, comprising from 2 to 50 ethylene oxide units, and mixtures thereof, in particular in the form of alkali metal salts, alkaline-earth metal salts, ammonium salts or amino alcohol salts. More preferentially, the anionic surfactant(s) are chosen from (C10-20) alkyl sulfates in the form of alkali metal or alkaline-earth metal salts, and in particular sodium lauryl sulfate and sodium cetostearyl sulfate, and mixtures thereof.

The amphoteric or zwitterionic surfactant(s) that may be used in the present invention may especially be optionally quaternized secondary or tertiary aliphatic amine derivatives, in which the aliphatic group is a linear or branched chain containing from 8 to 22 carbon atoms, the said amine derivatives containing at least one anionic group, for instance a carboxylate, sulfonate, sulfate, phosphate or phosphonate group. In particular, mention may be made of (C8-C20)alkylbetaines, sulfobetaines, (C8-C20 alkyl)amido(C3-C8 alkyl)betaines or (C8-C20 alkyl)amido(C6-C8 alkyl)sulfobetaines.

Among the optionally quaternized, secondary or tertiary aliphatic amine derivatives that can be used, as defined above, mention may also be made of the compounds having the respective structures (I) and (II) below:

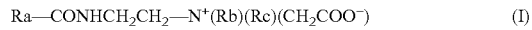

$$Ra\text{—}CONHCH_2CH_2\text{—}N^+(Rb)(Rc)(CH_2COO^-) \qquad (I)$$

in which:
Ra represents a $C_{10}$-$C_{30}$ alkyl or alkenyl group derived from an acid,
Ra—COOH, preferably present in hydrolysed coconut oil, represents a heptyl, nonyl or undecyl group,
Rb represents a β-hydroxyethyl group, and
Rc represents a carboxymethyl group;
and

$$Ra'\text{—}CONHCH_2CH_2\text{—}N(B)(B') \qquad (II)$$

in which:
B represents —$CH_2CH_2OX'$,
B' represents —$(CH_2)_z$—Y', with z=1 or 2,
X' represents the group —$CH_2$—COOH, $CH_2$—COOZ', —$CH_2CH_2$—COOH, —$CH_2CH_2$—COOZ', or a hydrogen atom,
Y' represents —COOH, —COOZ', the group —$CH_2$—CHOH—$SO_3H$ or —$CH_2$—CHOH—$SO_3Z'$,
Z' represents an ion derived from an alkali metal or alkaline-earth metal, such as sodium, an ammonium ion or an ion derived from an organic amine,
Ra' represents a C10-C30 alkyl or alkenyl group of an acid Ra'—COOH preferably present in hydrolysed coconut oil or hydrolysed linseed oil, an alkyl group, in particular a C17 alkyl group, and its iso form, or an unsaturated C17 group.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylamphodipropionate, disodium caryloamphodipropionate, lauroamphodipropionic acid and cocoamphodipropionic acid.

By way of example, mention may be made of the cocoamphodiacetate sold by the company Rhodia under the trade name Miranol® C2M Concentrate.

The amounts of surfactants present in the composition A according to the invention may range from 0.01% to 30%, preferably from 0.1% to 20% and better still from 0.5% to 10% by weight relative to the total weight of composition A.

Organic Inert Liquid Phase

The composition A in accordance with the invention may comprise at least one organic inert liquid phase.

For the purposes of the present invention, the term "liquid phase" means any phase that is capable of flowing at room temperature, generally between 15° C. and 40° C., and at atmospheric pressure, under the action of its own weight.

Examples of inert liquid phases that may be mentioned include the polydecenes of formula $C_{10n}H_{[(20n)+2]}$ in which n ranges from 3 to 9 and preferably from 3 to 7, esters of fatty alcohols or of fatty acids, sugar esters or diesters of $C_{12}$-$C_{24}$ fatty acids, cyclic esters, cyclic ethers, silicone oils, mineral oils and plant oils, or mixtures thereof.

The compounds of formula $C_{10n}H_{[(20n)+2]}$ in which n ranges from 3 to 9 correspond to the name "polydecene" of the CTFA dictionary, 7th edition, 1997 of the Cosmetic, Toiletry and Fragrance Association, USA, and also to the same INCI name in the USA and in Europe. These are poly-1-decene hydrogenation products.

Among these compounds, those for which, in the formula, n ranges from 3 to 7 are preferred.

Examples that may be mentioned include the products sold under the name Silkflo® 366 NF Polydecene by the company Amoco Chemical, and those sold under the name Nexbase® 2002 FG, 2004 FG, 2006 FG and 2008 FG by the company Fortum.

As regards the esters of fatty alcohols or of fatty acids, examples that may be mentioned include:

esters of saturated, linear or branched $C_3$-$C_6$ lower monoalcohols with monofunctional $C_{12}$-$C_{24}$ fatty acids, these fatty acids possibly being linear or branched, saturated or unsaturated and chosen especially from oleates, laurates, palmitates, myristates, behenates, cocoates, stearates, linoleates, linolenates, caprates and arachidonates, or mixtures thereof, and especially oleo-palmitates, oleo-stearates and palmito-stearates. Among these esters, it is more particularly preferred to use isopropyl palmitate, isopropyl myristate and octyldodecyl stearate, esters of linear or branched $C_3$-$C_8$ monoalcohols with difunctional $C_8$-$C_{24}$ fatty acids, these fatty acids possibly being linear or branched, and saturated or unsaturated, for instance the isopropyl diester of sebacic acid, also known as diisopropyl sebacate, esters of linear or branched $C_3$-$C_8$ monoalcohols with difunctional $C_2$-$C_8$ fatty acids, these fatty acids possibly being linear or branched, and saturated or unsaturated, for instance dioctyl adipate and dicaprylyl maleate, the ester of a trifunctional acid, for instance triethyl citrate.

As regards the sugar esters and diesters of $C_{12}$-$C_{24}$ fatty acids, the term "sugar" means compounds containing several alcohol functions, with or without an aldehyde or ketone function, and which comprise at least 4 carbon atoms. These sugars may be monosaccharides, oligosaccharides or polysaccharides.

As sugars that may be used according to the invention, examples that may be mentioned include sucrose (or saccharose), glucose, galactose, ribose, fucose, maltose, fructose, mannose, arabinose, xylose and lactose, and derivatives thereof, especially alkyl derivatives such as methyl derivatives, for instance methylglucose.

The sugar esters of fatty acids that may be used according to the invention may be chosen especially from the group comprising esters or mixtures of esters of sugars described above and of linear or branched, saturated or unsaturated $C_{12}$-$C_{24}$ fatty acids.

The esters may be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, especially, oleo-palmitate, oleo-stearate and palmito-stearate mixed esters.

It is more particularly preferred to use monoesters and diesters and especially sucrose, glucose or methyl-glucose mono- or dioleates, stearates, behenates, oleopalmitates, linoleates, linolenates and oleo-stearates.

An example that may be mentioned is the product sold under the name Glucate® DO by the company Amerchol, which is a methylglucose dioleate.

Examples of esters or mixtures of esters of sugar and of fatty acid that may also be mentioned include:

the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;

the products sold under the name Ryoto Sugar Esters, for example referenced B370 and corresponding to sucrose behenate formed from 20% monoester and 80% diester, triester and polyester;

the sucrose monodipalmitostearate sold by the company Goldschmidt under the name Tegosoft® PSE.

As regards the cyclic ethers and cyclic esters, γ-butyrolactone, dimethyl isosorbide and diisopropyl isosorbide are especially suitable.

Silicone oils may also be used as inert organic liquid phase.

More particularly, the silicone oils that are suitable are liquid, non-volatile silicone fluids with a viscosity of less than or equal to 10 000 mPa·s at 25° C., the viscosity of the silicones being measured according to ASTM standard 445 Appendix C.

Silicone oils are defined in greater detail in Walter Noll's "Chemistry and Technology of Silicones" (1968)—Academic Press.

Among the silicone oils that may be used according to the invention, mention may be made especially of the silicone oils sold under the names DC-200 Fluid—5 mPa·s, DC-200 Fluid—20 mPa·s, DC-200 Fluid—350 mPa·s, DC-200 Fluid—1000 mPa·s and DC-200 Fluid—10 000 mPa·s by the company Dow Corning.

Mineral oils may also be used as inert organic liquid phase, for instance liquid paraffin.

Plant oils may also be suitable for use, and especially avocado oil, olive oil or liquid jojoba wax.

Preferably, the inert organic liquid phase is preferably from the polydecenes of formula $C_{10n}H_{[(20n)+2]}$ in which n ranges from 3 to 9 and preferably from 3 to 7, and esters of fatty alcohols or of fatty acids, and mixtures thereof.

According to one particular embodiment of the invention, the content of inert organic liquid phase ranges from 0.1% to 30% by weight, preferably from 0.5% to 20% by weight and even more preferentially from 1% to 10% by weight relative to the weight of composition A.

According to one embodiment, composition A in compressed form comprises at least one hydrogen peroxide-generating agent.

As hydrogen peroxide-generating agents that are useful in the invention, mention may be made of polymeric complexes that can release hydrogen peroxide, such as polyvinylpyrrolidone/H2O2 in particular in the form of powders, and the other polymeric complexes described in U.S. Pat. No. 5,008,093; U.S. Pat. No. 3,376,110; U.S. Pat. No. 5,183,901; Mention may also be made of urea peroxide and alkali metal, alkaline-earth metal or ammonium perborates and percarbonates. Alkali metal or alkaline-earth metal percarbonates and in particular sodium percarbonate are preferably used.

It may be noted that alkali metal, alkaline-earth metal or ammonium persulfates are not included in these precursors since, in the redox mechanisms using these persulfates, there is no release of hydrogen peroxide.

In this embodiment, the hydrogen peroxide-generating agent(s) may represent from 0.1% to 40% by weight, preferably 0.5% to 20% by weight and better still from 1% to 10% by weight relative to the total weight of composition A.

Composition A in compressed form is anhydrous.

For the purposes of the invention, a composition is anhydrous when it has a water content of less than 1% by weight and preferably less than 0.5% by weight relative to the total weight of the composition. Preferably, composition A is free of water.

The composition A in accordance with the present invention may also comprise various additives conventionally used in cosmetics.

The composition in accordance with the present invention may thus comprise lubricants, for instance polyol stearates or alkali metal or alkaline-earth metal stearates, pigments, dyes, additives such as urea, ammonium chloride, antioxidants, penetrants, sequestrants such as EDTA or EDDS, buffers, dispersants, film-forming agents, preservatives, opacifiers, vitamins, fragrances, anionic, nonionic, amphoteric or zwitterionic polymers other than the rheology modifiers already mentioned, conditioning agents, for instance cationic polymers, cationic surfactants, ceramides and amino silicones.

Needless to say, a person skilled in the art will take care to select this or these optional additional compound(s) such that the advantageous properties intrinsically associated with the composition in accordance with the invention are not, or are not substantially, adversely affected by the envisaged addition(s).

Composition A in compressed form may be obtained according to known compression or compacting (or pelleting) processes, for instance direct compression. Composition A may especially be provided in the form of a powder that is compacted, for example in a pelletizer, by application of a compression force. The value of the compression force may range, for example, from 0.1 to 500 MPa and in particular from 0.2 to 100 MPa.

Composition A in compressed form may be a monolayer or multilayer composition.

According to one embodiment, it may comprise at least one layer comprising the bleaching composition comprising at least one persulfate and at least one "additional" layer which may comprise, for example, breakdown agents intended to accelerate the disintegration of the composition under compressed form, alkaline agents as mentioned above, and cosmetic active agents, and mixtures thereof. Breakdown agents that may especially be mentioned include celluloses and cellulose derivatives, crosslinked polyacrylates, crosslinked polyvinylpyrrolidone, gums, such as guar gum, soybean polysaccharides, alginates, aluminium silicates and derivatives thereof, and silicas, especially hydrophilic silicas, and mixtures thereof. According to one embodiment, composition A in compressed form comprises at least one layer comprising the bleaching composition comprising at least one persulfate, at least one additional layer comprising at least one breakdown agent intended to accelerate the disintegration of the composition, and at least one additional layer comprising at least one alkaline agent.

According to one embodiment, composition A in compressed form comprising at least one persulfate comprises at least one inclusion, for example in bead form, comprising a powder or a liquid encapsulated in a water-soluble film.

The composition in compressed form according to the invention may be in a ready-to-use single-dose form. According to one embodiment, it may be splittable and may comprise on at least one of its faces at least one splitting bar indicating a division of the composition into two parts (for example two halves) or several parts, in order to enable metering of the amount of bleaching composition A to be used in the process.

The composition in compressed form may be conditioned in individual form or grouped in a hermetic, moisture-proof sachet.

The bleaching process according to the present invention consists in applying to the keratin fibres composition A in compressed form as defined above, in the presence of an aqueous composition B.

Composition A in compressed form is generally added to the aqueous composition B just at the time of use, i.e. just before application to the keratin fibres. The step of dissolution of composition A in compressed form may take a few seconds to a few minutes, and may be performed with or without stirring.

A subject of the present invention is also a multi-compartment device comprising:
- at least one composition A that is in compressed form comprising at least one persulfate, and
- at least one aqueous composition B, the said compositions being conditioned separately.

Composition B

The suitable medium for the aqueous composition B comprising generally consists of water or a mixture of water and at least one organic solvent to dissolve the compounds that are not sufficiently water-soluble. Examples of organic solvents that may be mentioned include $C_1$-$C_4$ lower alkanols, such as ethanol and isopropanol; polyols such as propylene glycol, glycerol, dipropylene glycol and polyol ethers, for instance 2-butoxyethanol, propylene glycol monomethyl ether, and also aromatic alcohols, for instance benzyl alcohol or phenoxyethanol, similar products and mixtures thereof.

The solvents may be present in proportions preferably of between 1% and 40% by weight approximately and more preferably still between 5% and 30% by weight approximately relative to the total weight of composition B.

According to one embodiment, the aqueous composition B comprises at least one oxidizing agent.

The oxidizing agents that may be used in composition B are preferably chosen from hydrogen peroxide and compounds that release hydrogen peroxide by hydrolysis, such as urea peroxide. Hydrogen peroxide is preferably used.

The oxidizing agent may represent from 0.5% to 70% by weight, preferably from 1% to 60% by weight and better still from 5% to 20% by weight relative to the total weight of composition B.

The aqueous composition B comprising at least one oxidizing agent preferably has a pH of less than 7, the acidic pH ensuring the stability of the oxidizing agent in this composition.

The aqueous composition B may be in any form suitable to allow good dilution of composition A in compressed form, preferably in liquid form.

Composition B may also contain various additives conventionally used in cosmetics, such as those described previously.

It may also comprise agents for controlling the release of oxygen, such as magnesium carbonate or oxide.

The additives and the oxygen-release control agents as defined previously may be present in an amount, for each of them, of between 0.01% and 40% by weight and preferably between 0.1% and 30% by weight relative to the total weight of composition B.

The invention will be illustrated more fully with the aid of the non-limiting examples that follow. Unless otherwise mentioned, the amounts indicated are expressed in grams.

EXAMPLE

The following bleaching composition in powder form was prepared:

| | |
|---|---|
| Urea | 3 |
| Sodium persulfate | 8 |

-continued

| | |
|---|---|
| Ammonium chloride | 4.5 |
| Potassium persulfate | 47 |
| Ethylenediaminetetraacetic acid | 1 |
| Sodium metasilicate | 12 |
| Magnesium oxide | 1 |
| Kaolinite | 5 |
| Anatase titanium oxide | 2 |
| Vinylpyrrolidone/vinyl acetate copolymer (65/35) | 1.8 |
| Guar gum | 2.7 |
| Hydrogenated polydecene (MW 549) | 1.7 |
| Polyquaternium 5 (Merquat 5 from Nalco) | 1 |
| Cetylhydroxy cellulose (Natrosol Plus 330 CS from Ashland) | 1 |
| Copolymer of polyethylene glycol containing 136 mol of ethylene oxide, stearyl alcohol polyoxyethylenated with 100 mol of ethylene oxide and hexamethylene diisocyanate (HDI) (Rheolate FX 1100 ® from Elementis) | 3 |
| Sodium cetostearyl sulfate | 1 |
| Sodium lauryl sulfate | 2.3 |
| Magnesium stearate | 2 |

Tablets of 2 g each are prepared from the obtained powder using a Specac compacting machine, the compression force being 0.2 MPa.

The composition A in tablet form thus obtained can be mixed with a 40-volumes aqueous hydrogen peroxide composition B in a 1/1.5 ratio (i.e. 1 tablet per 3 g of composition B).

The invention claimed is:

1. A process for bleaching keratin fibers comprising applying to the keratin fibers a composition A that is in compressed form comprising at least one persulfate and at least one alkaline agent, in the presence of an aqueous composition B; wherein composition A, in compressed form, has at least one dimension greater than 6 mm.

2. A process according to claim 1, wherein the at least one persulfate is chosen from sodium, potassium and ammonium persulfates, and mixtures thereof.

3. A process according to claim 1, wherein the at least one persulfate is present in an amount ranging from about 10% to about 80% by weight relative to the total weight of composition A.

4. A process according to claim 1, wherein the at least one alkaline agent is chosen from water-soluble silicates, dibasic or tribasic alkali metal or alkaline-earth metal phosphates, and alkali metal or alkaline-earth metal carbonates, and mixtures thereof.

5. A process according to claim 4, wherein the at least one alkaline agent is chosen from alkali metal and alkaline earth metal silicates.

6. A process according to claim 1, wherein the at least one alkaline agent is present in an amount ranging from about 0.1% to about 40% by weight relative to the total weight of composition A.

7. A process according to claim 1, wherein composition A further comprises at least one rheology modifier chosen from hydrophilic thickeners, amphiphilic polymers comprising at least one hydrophobic chain, fillers, and mixtures thereof.

8. A process according to claim 7, wherein composition A comprises at least one hydrophilic thickener chosen from:
thickening polymers of natural origin,
synthetic polymers, and
mixtures thereof.

9. A process according to claim 8, wherein composition A comprises at least one hydrophilic thickener chosen from:
alkyl extracts, gums, guar gum and nonionic derivatives thereof, optionally modified starches, dextrins, optionally crosslinked celluloses and cellulose derivatives, pectins, chitosan and derivatives thereof, anionic polysaccharides other than starch and cellulose derivatives, soybean polysaccharides,
crosslinked or non-crosslinked polyvinylpyrrolidone, acrylic acid polymers and salts thereof, polyacrylamides, crosslinked or non-crosslinked poly-2-acrylamidopropanesulfonic acid polymers; and
mixtures thereof.

10. A process according to claim 7, wherein composition A comprises at least one amphiphilic polymer comprising at least one hydrophobic chain chosen from:
hydrophobic-chain nonionic amphiphilic polymers,
anionic amphiphilic polymers comprising at least one hydrophobic chain, and
mixtures thereof.

11. A process according to claim 10, wherein composition A comprises at least one amphiphilic polymer comprising at least one hydrophobic chain chosen from:
celluloses comprising a hydrophobic chain; hydroxypropyl guars modified with one or more hydrophobic groups; copolymers of vinylpyrrolidone and of hydrophobic-chain monomers; copolymers of $C_1$-$C_6$ alkyl (meth)acrylates and of amphiphilic monomers comprising a hydrophobic chain; copolymers of hydrophilic (meth)acrylates and of monomers comprising at least one hydrophobic chain (polyethylene glycol methacrylate/lauryl methacrylate copolymer); polymers with an aminoplast ether backbone bearing at least one fatty chain; linear, grafted or star polyether polyurethanes, comprising in their chain at least one hydrophilic block and at least one hydrophobic block;
crosslinked or non-crosslinked polymers comprising at least one hydrophilic unit derived from one or more ethylenically unsaturated monomers bearing a carboxylic acid function, which is free or partially or totally neutralized, and at least one hydrophobic unit derived from one or more ethylenically unsaturated monomers bearing a hydrophobic side chain, and optionally at least one crosslinking unit derived from one or more polyunsaturated monomers, which are crosslinked or non-crosslinked, and copolymers of (meth)acrylic acid and of fatty alcohol allyl ethers; and
mixtures thereof.

12. A process according to claim 7, wherein composition A comprises at least one filler chosen from mineral fillers, organic fillers, and mixtures thereof.

13. A process according to claim 12, wherein composition A comprises at least one filler chosen from silicas, clays, ceramic beads, calcium carbonate, titanium oxides, magnesium oxides, aluminium silicates and derivatives thereof, mixed silicates of natural or synthetic origin, which are optionally hydrated, natural hydrated aluminium silicates, bentonite, kaolin, Nylon, microspheres based on a copolymer of vinylidene chloride/acrylonitrile/methacrylonitrile containing isobutane, micronized or non-micronized vegetable powders, rice grain husk powders, and mixtures thereof.

14. A process according to claim 7, wherein the at least one rheology modifier is present in an amount ranging from about 0.01% to about 30% by weight relative to the total weight of composition A.

15. A process according to claim 1, wherein composition A comprises at least one agent chosen from celluloses and cellulose derivatives, crosslinked polyacrylates, crosslinked polyvinylpyrrolidone, gums, soybean polysaccharides, alginates, aluminium silicates and derivatives thereof, and hydrophilic silicas, and mixtures thereof.

16. A process according to claim 1, wherein composition A comprises at least one inert organic liquid.

17. A process according to claim 16, wherein the at least one inert organic liquid is chosen from polydecenes of formula $C_{10n}H_{[(20n)+2]}$, wherein n ranges from 3 to 9, and esters of fatty alcohols or of fatty acids, and mixtures thereof.

18. A process according to claim 1, wherein composition A comprises at least one surfactant.

19. A process according to claim 18, wherein the at least one surfactant is chosen from anionic and nonionic surfactants.

20. A process according to claim 1, wherein composition A comprises at least one hydrogen peroxide-generating agent.

21. A process according to claim 20, wherein the at least one hydrogen peroxide-generating agent is chosen from alkali metal and alkaline earth metal percarbonates.

22. A process according to claim 1, wherein composition B further comprises at least one oxidizing agent.

23. A process according to claim 22, wherein composition B comprises hydrogen peroxide.

24. A composition for bleaching keratin fibers, which is in compressed form, comprising at least one persulfate, at least one alkaline agent, and at least one water-soluble silicate; wherein composition A, in compressed form, has at least one dimension greater than 6 mm.

* * * * *